United States Patent [19]

Haga et al.

[11] Patent Number: 4,595,409
[45] Date of Patent: Jun. 17, 1986

[54] SUBSTITUTED PHENYL-4,5,6,7-TETRAHYDRO-2H-ISOINDOLE-1,3-DIONES, AND THEIR PRODUCTION AND USE

[75] Inventors: Toru Haga, Ibaraki; Eiki Nagano, Nishinomiya; Ryo Yoshida, Kawanishi, all of Japan; Shunichi Hashimoto, Leland, Miss.

[73] Assignee: Sumitomo Chemical Company, Ltd., Osaka, Japan

[21] Appl. No.: 638,680

[22] Filed: Aug. 8, 1984

[30] Foreign Application Priority Data

Aug. 31, 1983 [JP] Japan ............... 58-160855

[51] Int. Cl.$^4$ ................... A01N 43/38; C07D 209/48
[52] U.S. Cl. ......................... 71/96; 548/513
[58] Field of Search ............... 548/513; 71/95, 96; 564/162, 440; 560/17; 260/455 R

[56] References Cited

U.S. PATENT DOCUMENTS

| 3,235,605 | 2/1966 | Napolitano ............... 564/440 |
| 3,465,001 | 9/1969 | Bolhoffer et al. . |
| 3,878,224 | 4/1975 | Matsui et al. . |
| 3,954,442 | 5/1976 | Becker et al. ............ 560/17 |
| 3,984,435 | 10/1976 | Matsui et al. . |
| 4,001,272 | 1/1977 | Goddard . |
| 4,032,326 | 6/1977 | Goddard . |
| 4,124,375 | 11/1978 | Bollinger et al. ............ 71/96 |
| 4,349,377 | 9/1982 | Durr et al. ............ 560/17 |
| 4,431,822 | 2/1984 | Nagano et al. . |
| 4,439,229 | 3/1984 | Swithenbank ............ 71/95 |
| 4,484,940 | 11/1984 | Nagano et al. . |
| 4,484,941 | 11/1984 | Nagano et al. . |
| 4,536,209 | 8/1985 | Jikihara . |

FOREIGN PATENT DOCUMENTS

| 0061741 | 3/1982 | European Pat. Off. . |
| 0049508 | 4/1982 | European Pat. Off. . |
| 0068822 | 6/1982 | European Pat. Off. . |
| 0083055 | 12/1982 | European Pat. Off. . |
| 0077938 | 4/1983 | European Pat. Off. . |
| 0126419 | 11/1984 | European Pat. Off. . |
| 55-130954 | 10/1980 | Japan . |
| 57-24355 | 2/1982 | Japan . |
| 2046754 | 4/1980 | United Kingdom . |
| 213814 | 8/1968 | U.S.S.R. . |

OTHER PUBLICATIONS

Chemical Abstract 89:42719j.
Chemical Abstract 98:215478w.
Chemical Abstract 93:114150z.
Chemical Abstract 101:146132v.
Chemical Abstract 101:124918d.
Chemical Abstract 101:124919e.

*Primary Examiner*—Veronica P. Hoke
*Attorney, Agent, or Firm*—Birch, Stewart, Kolasch & Birch

[57] ABSTRACT

A compound of the formula:

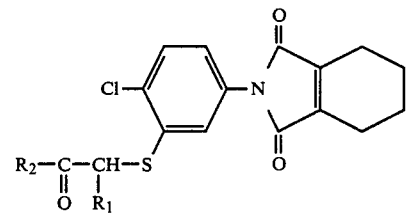

wherein $R_1$ is a hydrogen atom, a fluorine atom or a methyl group and $R_2$ is a $C_1$-$C_3$ alkyl group, a $C_1$-$C_5$ alkoxy group, a chloro($C_2$-$C_4$)alkoxy group, a dichloro($C_2$-$C_4$)alkoxy group, a cyclo($C_3$-$C_7$)alkoxy group, a phenoxy group, a $C_1$-$C_5$ alkylthio group or a di($C_1$-$C_5$)alkylamino group, which is useful as a herbicide.

13 Claims, No Drawings

SUBSTITUTED PHENYL-4,5,6,7-TETRAHYDRO-2H-ISOINDOLE-1,3-DIONES, AND THEIR PRODUCTION AND USE

The present invention relates to 2-substituted phenyl-4,5,6,7-tetrahydro-2H-isoindole-1,3-diones (hereinafter referred to as "isoindole(s)"), and their production and use.

The said isoindoles are representable by the formula:

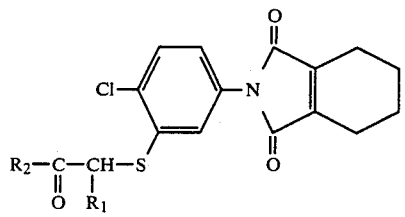

wherein $R_1$ is a hydrogen atom, a fluorine atom or a methyl group and $R_2$ is a $C_1$–$C_3$ alkyl group, a $C_1$–$C_5$ alkoxy group, a chloro($C_2$–$C_4$)alkoxy group, a dichloro($C_2$–$C_4$)alkoxy group, a cyclo($C_3$–$C_7$)alkoxy group, a phenoxy group, a $C_1$–$C_5$ alkylthio group or a di($C_1$–$C_5$)alkylamino group.

It is known that certain kinds of isoindoles are effective as herbicides. For instance, the herbicidal use of 2-(4-chlorophenyl)-4,5,6,7-tetrahydro-2H-isoindole-1,3-dione, 2-(4-chloro-3-ethoxycarbonylmethoxyphenyl)-4,5,6,7-tetrahydro-2H-isoindole-1,3-dione and 2-(4-chloro-3-ethoxycarbonylmethylaminophenyl)-4,5,6,7-tetrahydro-2H-isoindole-1,3-dione is disclosed in U.S. Pat. No. 3,878,224, EP-No. 0049508A and EP-No. 0007938A. However, their herbicidal effect is not necessarily satisfactory.

It has now been found that the isoindoles (I) show a strong herbicidal activity against a wide variety of weeds including broad-leaved weeds, Graminaceous weeds and Cyperaceae weeds in agricultural plowed field by foliar or soil treatment and do not produce any material phytotoxicity on various agricultural crops (i.e. corn, wheat, rice plant, soybean). Examples of broad-leaved weeds are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), garden radish (*Raphanus sativus*), hemp sesbania (*Sesbania exaltata*), sicklepod (*Cassia tora*), velvetleaf (*Abutilon theophrasti*), prickly sida (*Sida spinosa*), field pansy (*Viola arvensis*), wild carrot (*Daucus carota*), catchweed bedstraw (*Galium aparine*), ivyleaf morningglory (*Ipomoea hederifolia*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum nigrum*), birdseye speedwell (*Veronica persica*), ivyleaf speedwell (*Veronica hederaefolia*), heartleaf cocklebur (*Xanthium strumarium*), common sunflower (*Helianthus annuus*), scentless chamomile (*Matricaria inodola*), corn marigold (*Chrysnathemum segetum*), etc. Examples of Graminaceous weeds against which the isoindoles (I) show a herbicidal activity are Japanese millet (*Echinochloa frumentacea*), common barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), common oat (*Avena sativa*), etc. Examples of Cyperaceae weeds are rice flatsedge (*Cyperus iria*), etc. Further, they are also useful in controlling or exterminating in the paddy field the broadleaved weeds such as barnyardgrass (*Echinochloa oryzicola*), broad-leaved weeds such as common falsepimpernel (*Lindernia procumbens*), toothcup (*Rotala indica*), waterwort (*Elatine triandra*), Cyperaceous weeds such as umbrella plant (*Cyperus difformis*), hardstem bulrush (*Scirpus juncoides*), slender spikerush (*Eleocharis acicularis*), water nutsedge (*Cyperus serotinus*) and the paddy-field weeds such as pickerelweed (*Monochoria vaginalis*), arrowhead (*Sagittaria pygmaea*), while exerting no material phytotoxicity to rice plants. Accordingly, the isoindoles (I) can be used as herbicides applicable to agricultural plowed field as well as paddy field.

Among the isoindoles (I) of the invention, those wherein $R_1$ is a hydrogen atom and $R_2$ is a $C_1$–$C_5$ alkoxy group, a chloro($C_2$–$C_4$)alkoxy group, a dichloro($C_2$–$C_4$)alkoxy group, a cyclo($C_3$–$C_7$)alkoxy group, a phenoxy group or a $C_1$–$C_5$ alkylthio group are preferable in view of their prominent herbicidal activity as well as their scarce phototoxicity to crop plants. They hardly exert a chemical injury to soybeans and corn on foliar treament in the plowed field.

The isoindole (I) is obtainable by reacting 2-(4-chloro-3-hydrothiophenyl)-4,5,6,7-tetrahydro-2H-isoindole-1,3-dione with a compound of the formula:

wherein $R_1$ and $R_2$ are each as defined above and Y is a chlorine atom, a bromine atom or an iodine atom.

The reaction is usually carried out in a solvent in the presence of a dehydrohalogenating agent with or without a phase transfer catalyst at a temperature of about 70° to 100° C. for a period of 1 to 24 hours. The amounts of the compound (II) and the dehydrohalogenating agent may be respectively from 1 to 5 equivalents and from 1 to 10 equivalents to the starting 2-(4-chloro-3-hydrothiophenyl)-4,5,6,7-tetrahydro-2H-isoindole-1,3-dione.

Examples of the solvent are aliphatic hydrocarbons (e.g. hexane, heptane, ligroin), aromatic hydrocarbons (e.g. benzene, toluene, xylene), halogenated hydrocarbons (e.g. dichloroethane, chlorobenzene, dichlorobenzene), ethers (e.g. diisopropyl ether, dioxane, diethylene glycol dimethyl ether), ketones (e.g. acetone, methyl ethyl ketone, methyl isobutyl ketone, isophorone, cyclohexanone), nitriles (e.g. acetonitrile, isobutyronitrile), acid amides (e.g. formamide, N,N-dimethylformamide, acetamide), sulfur compounds (e.g. dimethylsulfoxide, sulfolane), water. They may be used alone or in combination. Examples of the dehydrohalogenating agents are organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc. As the phase transfer catalyst, there may be used tetra-n-butylammonium bromide, benzyltri-n-butylammonium chloride, etc.

The reaction mixture may be subjected to ordinary post-treatment such as extraction or condensation to recover the produced isoindole (I). When desired, the product may be further purified by a per se conventional procedure such as column chromatography or recrystallization.

A typical example for the production of the isoindoles (I) is as follows:

EXAMPLE 1

A suspension of 2-(4-chloro-3-hydrothiophenyl)-4,5,6,7-tetrahydro-2H-isoindole-1,3-dione (1.5 g) and tetran-butylammonium bromide (0.2 g) in a 5% potassium hydroxide solution (9 ml) was heated to 80° to 90° C., and 2,2-dichloroethyl bromoacetate (3.5 g) was dropwise added thereto at 80° to 90° C. The resultant mixture was heated at the same temperature for 1 hour and allowed to cool. The reaction mixture was diluted with water and extracted with toluene. Toluene was removed under reduced pressure, and the residue was purified by silica gel column chromatography using a mixture of ethyl acetate and n-hexane (1:4) as an eluent to give 0.6 g of 2-[4-chloro-3-(2,2-dichloroethyloxycarbonylmethylthio)phenyl]-4,5,6,7-tetrahydro-2H-isoindole-1,3-dione. $n_D^{28.0}$ 1.5897.

In the same manner as above, there were produced other isoindoles (I), of which typical examples are as shown in Table 1.

TABLE 1

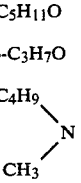

| Compound No. | $R_1$ | $R_2$ | Physical constant |
|---|---|---|---|
| 1 | H | Cl$_2$CHCH$_2$O | $n_D^{28.0}$ 1.5897 |
| 2 | H | ClCH$_2$CH$_2$O | $n_D^{29.7}$ 1.5987 |
| 3 | H | n-C$_5$H$_{11}$O | $n_D^{30.5}$ 1.5482 |
| 4 | H | iso-C$_3$H$_7$O | $n_D^{30.5}$ 1.5932 |
| 5 | CH$_3$ | n-C$_4$H$_9$\N/CH$_3$ | $n_D^{29.7}$ 1.5538 |
| 6 | CH$_3$ | n-C$_5$H$_{11}$S | $n_D^{30.5}$ 1.5682 |
| 7 | H | iso-C$_3$H$_7$S | $n_D^{30.5}$ 1.5932 |
| 8 | H | —O | $n_D^{29.7}$ 1.5785 |
| 9 | H | C$_2$H$_5$O | $n_D^{25.7}$ 1.5758 |
| 10 | H | CH$_3$O | M.P. 106.3° C. |
| 11 | H | —O | $n_D^{20.4}$ 1.5784 |
| 12 | H | C$_6$H$_5$O | M.P. 120.1° C. |
| 13 | H | CH$_3$ | M.P. 166.5° C. |
| 14 | F | C$_2$H$_5$O | $n_D^{19.2}$ 1.5871 |

The starting 2-(4-chloro-3-hydrothiophenyl)-4,5,6,7-tetrahydro-2H-isoindole-1,3-dione is obtainable by reacting 2-chloro-5-aminothiophenol with 1 to 3 equivalents of 3,4,5,6-tetrahydrophthalic anhydride in a solvent at a temperature of 90° to 120° C. for 1 to 24 hours. As the solvent, there may be employed aliphatic hydrocarbons (e.g. hexane, ligroin), aromatic hydrocarbons (e.g. benzene, toluene, xylene), ethers (e.g. diisopropyl ether, dioxane, diethylene glycol dimetyl ether), aliphatic acids (e.g. acetic acid, propionic acid), water, or a mixture thereof. After completion of the reaction, the reaction mixture is subjected to ordinary post-treatment such as extraction, condensation or precipitation. The thus obtained product may be, if necessary, purified by a per se conventional procedure such as column chromatography or recrystallization.

A typical example for production of 2-(4-chloro-3-hydrothiophenyl)-4,5,6,7-tetrahydro-2H-isoindole-1,3-dione is as follows:

EXAMPLE 2

2-Chloro-5-aminobenzenethiol (21.1 g) and tetrahydrophthalic anhydride (20.4 g) were dissolved in acetic acid (130 ml), and the resultant mixture was heated at 100° to 110° C. for 1 hour while stirring. The reaction mixture was allowed to cool and diluted with water. The precipitated crystals were collected by filtration and washed with ethanol to give 28.2 g of 2-(4-chloro-3-hydrothiophenyl)-4,5,6,7-tetrahydro-2H-isoindole-1,3-dione. M.P., 153°–155° C.

2-Chloro-5-aminothiophenol may be produced by reacting 2-chloro-5-nitrobenzenesulfonyl chloride with stannous chloride and hydrochloric acid or with zinc and hydrochloric acid or sulfuric acid at a temperature of 40° to 100° C. The amount of the stannous chloride or zinc is usually from 6 to 10 equivalents to 2-chloro-5-nitrobenzenesulfonyl chloride.

After completion of the reaction, the reaction mixture is subjected to post-treatment, for instance, addition of conc. hydrochloric acid and collection of the precipitate. If necesary the collected product may be further purified by a per se conventional procedure such as chromatography or recrystallization.

A typical example for production of 2-chloro-5aminothiophenol is as follows:

EXAMPLE 3

A solution of anhydrous stannous chloride (152.5 g) in conc. hydrochloric acid (150 ml) was cooled to 0° C., and 2-chloro-5-nitrobenzenesulfonyl chloride (34.3 g) was added thereto while stirring. The resultant mixture was heated at 100° C. for 15 minutes while stirring, followed by being allowed to stand. Conc. hydrochloric acid (230 ml) was added to the reaction mixture. The precipitated crystals were collected by filtration, neutralized with a 4% aqueous sodium carbonate solution and extracted with ethyl acetate. The organic layer was dried and concentrated to give 25.0 g of 2-chloro-5-aminothiophenol. M.P., 68.3° C.

On the practical usage of the isoindole (I) as a herbicide, it may be applied as such or in any preparation form such as emulsifiable concentrate, wettable powder, suspension, granules, etc. in combination with a conventional solid or liquid carrier or diluent, a surface active agent and/or an auxiliary agent.

The content of the isoindole (I) as the active ingredient in said preparation form may be usually within a range of 0.03 to 90% by weight, preferably of 0.05 to 80% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc. The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, alginates, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

FORMULATION EXAMPLE 1

Thirty parts of Compound No. 1, 5 parts of calcium ligninsulfonate, 3 parts of sodium laurylsulfate and 62 parts of synthetic hydrated silicon dioxide are well mixed to obtain a wettable powder.

FORMULATION EXAMPLE 2

Ten parts of Compound No. 3, 14 parts of polyoxyethylenestyrylphenyl ether, 6 parts of calcium dodecylbenzenesulfonate, 30 parts of xylene and 40 parts of cyclohexanone are well mixed to obtain an emulsifiable concentrate.

FORMULATION EXAMPLE 3

Two parts of Compound No. 2, 1 part of synthetic hydrated silicon dioxide, 2 parts of calcium ligninsulfonate, 30 parts of bentonite and 65 parts of kaolin clay are well mixed. The mixture is then kneaded with water, granulated and dried to obtain granules.

FORMULATION EXAMPLE 4

Twenty-five parts of Compound No. 6 is mixed with 3 parts of polyoxyethylene sorbitan monooleate, 3 parts of CMC (carboxymethyl cellulose) and 69 parts of water, and the mixture is pulverized until the particle size of the mixture becomes less than 5 microns to obtain a suspension.

The isoindoles (I) thus formulated in any suitable formulation form are useful for the pre-emergence or postemergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the isoindole (I) over the top of plants. It may also be applied directly to weeds with care so as to keep the chemical off the crop foliage.

The isoindoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Besides, the isoindoles (I) can be used as herbicides applicable to agricultural plowed field as well as paddy field. They are also useful as herbicides to be employed for orchard, pasture land, lawn, forest, nonagricultural field, etc.

The dosage rate of the isoindoles (I) may vary on prevailing weather conditions, preparation used, prevailing season, mode of application, soil involved, crop and weed species, etc. Generally, however, the dosage rate may be from 0.05 to 50 grams, preferably from 0.2 to 20 grams, of the active ingredient per are. The herbicidal composition the invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological effect of the isoindoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below were used for comparison.

TABLE 2

| Compound No. | Chemical structure | Remarks |
| --- | --- | --- |
| A | (structure: Cl-phenyl-N-bicyclic diketone) | U.S. Pat. No. 3,878,224 |
| B | (structure: F$_3$C-phenyl(Cl)-O-phenyl(NO$_2$)-COONa) | acifluorfen (Na salt; commercially available herbicide) |
| C | (structure: Cl-phenyl(C$_2$H$_5$OCCH$_2$O-)-N-bicyclic diketone) | EP-0049508A |

TABLE 2-continued

| Compound No. | Chemical structure | Remarks |
| --- | --- | --- |
| D | Cl—[phenyl with C₂H₅OCCH₂NH (with =O) substituent]—N[ring with two =O groups, fused cyclohexane] | EP-0007938A |

TEST EXAMPLE 1

Plastic pots (diameter, 10 cm; height, 10 cm) were filled with upland field soil, and the seeds of Japanese millet, wild oat, garden radish and velvetleaf were sowed therein and covered with the soil. The test plants were cultivated in a greenhouse for 10 days. Thereafter, a designed amount of the test compound formulated into an emulsifiable concentrate according to Formulation Example 2 and diluted with water containing a spreading agent was sprayed over the top to the soil surface at a spray volume of 10 liters per are by means of a small hand sprayer. After 20 days cultivation in the greenhouse, the herbicidal activity on the plants was examined. The results are shown in Table 3.

TABLE 3

| Compound No. | Dosage (g/are) | Japanese millet | Wild oat | Garden radish | Velvetleaf |
| --- | --- | --- | --- | --- | --- |
| 1 | 20 | 5 | 5 | 5 | 5 |
| 2 | 20 | 5 | 5 | 5 | 5 |
| 3 | 20 | 5 | 5 | 5 | 5 |
| 4 | 20 | 5 | 5 | 5 | 5 |
| 5 | 20 | 5 | 5 | 5 | 5 |
| 6 | 20 | 5 | 5 | 5 | 5 |
| 7 | 20 | 5 | 5 | 5 | 5 |
| 8 | 20 | 5 | 5 | 5 | 5 |
| 9 | 20 | 5 | 5 | 5 | 5 |
| 10 | 20 | 5 | 5 | 5 | 5 |
| 11 | 20 | 5 | 5 | 5 | 5 |
| 12 | 20 | 5 | 4 | 5 | 5 |
| 13 | 20 | 5 | 5 | 5 | 5 |
| 14 | 20 | 5 | 4 | 5 | 5 |
| A | 20 | 3 | 3 | 4 | 5 |

TEST EXAMPLE 2

Vats (33 cm × 23 cm × 11 cm) were filled with upland field soil and the seeds of soybean, cotton, tall morningglory, heartleaf cocklebur, velvetleaf, common lambsquarters, corn, wheat, common barnyardgrass and green foxtail were sowed therein and the soil was covered to the depth of 1 to 2 cm. A designed amount of the test compound formulated into an emulsifiable concentrate according to Formulation Example 2 and diluted with water was sprayed to the soil surface by means of a small hand sprayer at a spray volume of 10 liters per are. After 20 days cultivation in a greenhouse, the herbicidal activity was examined. The results are shown in Table 4.

TABLE 4

| Compound No. | Dosage (g/are) | Soybean | Cotton | Tall morningglory | Heartleaf cocklebur | Velvetleaf | Common lambsquarters | Corn | Wheat | Common barnyardgrass | Green foxtail |
| --- | --- | --- | --- | --- | --- | --- | --- | --- | --- | --- | --- |
| 1 | 20 | 0 | 4 | 4 | 4 | 5 | 5 | 2 | 1 | 2 | 4 |

TEST EXAMPLE 3

Vats (33 cm × 23 cm × 11 cm) were filled with upland field soil and the seeds of soybean, cotton, tall morningglory, heartleaf cocklebur, velvetleaf, common lambsquarters, corn, wheat, common barnyardgrass and green foxtail were sowed therein and cultivated in a greenhouse. A designed amount of the test compound formulated into an emulsifiable concentrate according to Formulation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity was examined. At the time of the application, the growing stage of the test plants varied depending on their species but, they were generally at the 1 to 4 leaf stage and in 2 to 12 cm height. The results are shown in Table 5.

TABLE 5

| Compound No. | Dosage (g/are) | Soybean | Cotton | Tall morningglory | Heartleaf cocklebur | Velvetleaf | Common lambsquarters | Corn | Wheat | Common barnyardgrass | Green foxtail |
| --- | --- | --- | --- | --- | --- | --- | --- | --- | --- | --- | --- |
| 1 | 1.25 | 2 | 5 | 5 | 5 | 5 | 5 | 3 | 2 | 2 | 4 |
|   | 0.32 | 0 | 5 | 5 | 5 | 5 | 5 | 1 | 0 | 1 | 2 |
| 2 | 1.25 | 2 | 5 | 5 | 5 | 5 | 5 | 2 | 1 | 2 | 3 |
|   | 0.32 | 1 | 5 | 5 | 5 | 5 | 5 | 1 | 1 | 1 | 2 |
| 3 | 1.25 | 2 | 5 | 5 | 5 | 5 | 5 | 2 | 1 | 2 | 2 |
|   | 0.32 | 1 | 5 | 5 | 5 | 5 | 5 | 1 | 1 | 1 | 2 |
| 9 | 1.25 | 2 | 5 | 5 | 5 | 5 | 5 | 3 | 1 | 2 | 0 |
|   | 0.32 | 2 | 5 | 5 | 5 | 5 | 5 | 2 | 1 | 1 | 0 |
| A | 1.25 | 1 | 2 | 3 | 2 | 5 | 5 | 1 | 0 | 1 | 0 |
|   | 0.32 | 0 | 0 | 1 | 1 | 3 | 4 | 0 | 0 | 0 | 0 |
| B | 2.5 | 2 | 2 | 5 | 4 | 2 | 5 | 0 | 1 | 2 | 0 |
|   | 0.63 | 0 | 1 | 3 | 1 | 0 | 3 | 0 | 0 | 0 | 0 |
| C | 1.25 | 2 | 5 | 4 | 4 | 5 | 5 | 1 | 1 | — | — |

TABLE 5-continued

| Compound No. | Dosage (g/are) | Herbicidal activity | | | | | | | | |
|---|---|---|---|---|---|---|---|---|---|---|
| | | Soybean | Cotton | Tall morning-glory | Heart-leaf cocklebur | Velvet-leaf | Common lambs-quarters | Corn | Wheat | Common barn-yard-grass | Green fox-tail |
| | 0.32 | 1 | 5 | 2 | 2 | 4 | 3 | 0 | 0 | — | — |
| D | 1.25 | 4 | 5 | 5 | 5 | 5 | — | 3 | 2 | 2 | 0 |
| | 0.32 | 3 | 5 | 3 | 3 | 5 | — | 3 | 1 | 1 | 0 |

TEST EXAMPLE 4

Cylindrical plastic pots (diameter, 8 cm; height, 12 cm) were filled with paddy field soil, and the seeds of barnyardgrass, broad-leaved weeds (e.g. common false-pimpernel, toothcup, waterwort) and hardstem bulrush and the buds of arrowhead were sowed in 1 to 2 cm depth. Water was poured therein to make a flooded condition. Rice seedlings of the 2-leaf stage were transplanted therein and grown in a greenhouse. Six days thereafter, a designed amount of the test compound formulated in an emulsifiable concentrate according to Formulation Example 2 and diluted with water (5 ml) was applied to the pots by perfusion. The test plants were grown for further 20 days in the greenhouse, and the herbicidal activity was examined. The results are shown in Table 6.

TABLE 6

| Compound No. | Dosage (g/are) | Herbicidal activity | | | |
|---|---|---|---|---|---|
| | | Rice plant | Barn-yard-grass | Broad-leaved weed | Hardstem bulrush | Arrow-head |
| 1 | 20 | 1 | 4 | 5 | 4 | 4 |
| 3 | 20 | 1 | 4 | 5 | 3 | 5 |

What is claimed is:

1. A compound of the formula:

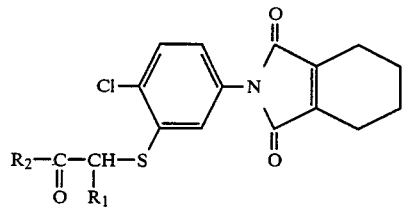

wherein $R_1$ is a hydrogen atom, a fluorine atom or a methyl group and $R_2$ is a $C_1$–$C_3$ alkyl group, a $C_1$–$C_5$ alkoxy group, a chloro($C_2$–$C_4$)alkoxy group, a dichloro($C_2$–$C_4$)alkoxy group, a cyclo($C_3$–$C_7$)alkoxy group, a phenoxy group, a $C_1$–$C_5$ alkylthio group or a di($C_1$–$C_5$)alkylamino group.

2. The compound according to claim 1, wherein $R_1$ is a hydrogen atom and $R_2$ is a $C_1$–$C_5$ alkoxy group, a chloro($C_2$–$C_4$)alkoxy grup, a dichloro($C_2$–$C_4$)alkoxy group, a cyclo($C_3$–$C_7$)alkoxy group, a phenoxy group or a $C_1$–$C_5$ alkylthio group.

3. The compound according to claim 1, which is 2-[4-chloro-3-(2-chloroethyloxycarbonylmethylthio)-phenyl]-4,5,6,7-tetrahydro-2H-isoindole-1,3-dione.

4. The compound according to claim 1, which is 2-(4-chloro-3-cyclopentyloxycarbonylmethylthio-phenyl)-4,5,6,7-tetrahydro-2H-isoindole-1,3-dione.

5. The compound according to claim 1, which is 2-(4-chloro-3-cyclohexyloxycarbonylmethylthio-phenyl)-4,5,6,7-tetrahydro-2H-isoindole-1,3-dione.

6. A process for producing the compound according to claim 1, which comprises reacting 2-(4-chloro-3-hydrothiophenyl)-4,5,6,7-tetrahydro-2H-isoindole-1,3-dione with a compound of the formula:

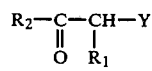

wherein $R_1$ and $R_2$ are each as defined in claim 1 and Y is a chlorine atom, a bromine atom or an iodine atom.

7. A herbicidal composition which comprises as an active ingredient a herbicidally effective amount of the compound according to claim 1, and an inert carrier or diluent.

8. A method for controlling weeds which comprises applying a herbicidally effective amount of the compound according to claim 1 to the area where the weeds grow or will grow.

9. The method according to claim 8, wherein the area is the field of soybean or corn.

10. 2-(4-Chloro-3-hydrothiophenyl)-4,5,6,7-tetrahydro-2H-isoindole-1,3-dione.

11. A herbicidal composition which comprises as an active ingredient a herbicidally effective amount of the compound according to claim 4, and an inert carrier or diluent.

12. A method for controlling weeds which comprises applying a herbicidally effective amount of the compound according to claim 4 to the area where the weeds grow or will grow.

13. The method according to claim 12, wherein the area is a field of soybean or corn.

* * * * *